(12) United States Patent
Itou et al.

(10) Patent No.: US 7,743,918 B2
(45) Date of Patent: Jun. 29, 2010

(54) CATHETER PACKAGE

(75) Inventors: Yasushi Itou, Fujinomiya (JP); Jun Iwami, Fujinomiya (JP); Shigeki Numata, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 218 days.

(21) Appl. No.: 10/594,727

(22) PCT Filed: Mar. 30, 2005

(86) PCT No.: PCT/JP2005/006145

§ 371 (c)(1),
(2), (4) Date: Sep. 29, 2006

(87) PCT Pub. No.: WO2005/094929

PCT Pub. Date: Oct. 13, 2005

(65) Prior Publication Data

US 2007/0197998 A1    Aug. 23, 2007

(30) Foreign Application Priority Data

Mar. 31, 2004    (JP)    ............................. 2004-107528

(51) Int. Cl.
*B65D 83/10* (2006.01)
(52) U.S. Cl. .................................................. 206/364
(58) Field of Classification Search ................ 604/533; 264/364
See application file for complete search history.

(56) References Cited

U.S. PATENT DOCUMENTS

| 4,850,954 A |   | 7/1989  | Charvin |
| 4,925,448 A | * | 5/1990  | Bazaral ...................... 604/171 |
| 5,165,540 A | * | 11/1992 | Forney ....................... 206/364 |
| 5,322,163 A | * | 6/1994  | Foos .......................... 206/364 |
| 5,501,341 A | * | 3/1996  | Van Es ....................... 206/364 |
| 5,947,296 A |   | 9/1999  | Castora |
| 6,508,806 B1 | * | 1/2003 | Hoste ......................... 604/524 |

FOREIGN PATENT DOCUMENTS

| GB | 2 371 036 A | 7/2002 |
| JP | 11-130132 A | 5/1999 |
| JP | 2000-281144 A | 10/2000 |

OTHER PUBLICATIONS

International Search Report dated Jul. 19, 2005.

* cited by examiner

*Primary Examiner*—Kevin C Sirmons
*Assistant Examiner*—Bradley J Osinski
(74) *Attorney, Agent, or Firm*—Buchanan Ingersoll & Rooney PC

(57) ABSTRACT

A package for a catheter that holds the distal part of the catheter in a natural state and the proximal part of the catheter in a curled state. The package is comprised of two trays that are bridged by the catheter and are held together by a slidable fixing member.

3 Claims, 10 Drawing Sheets

CATHETER PACKAGE

This is a 371 application of PCT/JP05/06145 filed Mar. 30, 2005. This application also claims priority to Japanese Ser. No. 2004-107528 filed Mar. 31, 2004.

TECHNICAL FIELD

The present invention relates to a package packing a catheter utilized for procedures, such as diagnosis and therapy, conducted by use of catheters.

BACKGROUND ART

Procedures such as diagnosis and therapy conducted using catheters have been spreading in recent years, since they involve less burden on the patient, as compared with elaborate procedures under general anesthesia. Such a minimally invasive procedure is conducted by introducing catheters and other various devices through a puncture hole formed at an arm, a leg or the like of the patient so as to penetrate into an artery. In addition, during the procedure, the conditions inside a blood vessel of the patient are observed through radiographic imaging. Specifically, the patient is laid on an imaging apparatus for displaying an image by receiving X-rays, and is irradiated with X-rays from above.

In such a surgery, a very wide variety of medical devices and medicines are used, e.g. devices used in the preparatory stage before surgery, such as throw-away nonwoven fabric (drape) laid on the imaging apparatus, an instillation set including a set of needle and tubes for dropping heparin as an antithrombic into the patient, and medicines such as disinfectant; medical doctor's procedure clothing, gloves, covers for shoes, masks, absorptive cotton for applying the disinfectant, etc. and devices used in the starting stage of surgery, such as tweezers, forceps, scissors; a skin cutting knife and an indwelling needle; devices used for diagnosis or therapy stage, such as an introducer sheath, a dilator, a guide wire for introducer, a syringe, an angiography catheter, a guide wire for the angiography catheter, angiographic medium, a microcatheter, a PTCA (percutaneous transluminal coronary angioplasty) guiding catheter (in the shapes for cardiac right-side coronary artery and for cardiac left-side coronary artery or the like), a guide wire for PTCA, a PTCA balloon catheter, a balloon inflator (indeflator), a stent with delivery catheter; devices used for after surgery stage, such as a hemostatic devices; other devices such as beakers, cups and the like for temporary storage of medicines, etc. Besides, for prevention of infection, most of these devices are disposable.

Conventionally, the above-mentioned devices are preliminarily placed on a table or a wagon with casters by a nurse. However, the nurse who, unlike the medical doctor, does not undergo scrupulous disinfection is permitted to touch those packaging surfaces of the devices which are exposed to the out but is not permitted to directly touch those devices inside the packages which may make contact with the patient's blood. On the other hand, the medical doctor who will engage directly in the surgery is permitted to directly touch the devices but is not permitted to touch the packaging surfaces which are exposed to the out.

Therefore, in the preparatory state, the nurse has been required to carry out very elaborate works, such as taking the devices out of the packages in a remote manner by use of forceps or the like means. In addition, the supplies work for purchasing and preparing the large number of devices has also been very troublesome.

Under the above-mentioned circumstances, there has been a movement to collectively envelope the devices to be used until the preparatory stage of a catheter procedure into a tray to form a kit, thereby simplifying the labor for purchase and layout and preventing misuse and mis-preparation. Meanwhile, in order to envelop a long catheter of more than 70 cm in length in such a tray, there is no other method than making round the catheter. However, since a braid of stainless steel wire is embedded in an angiography catheter or a PTCA guiding catheter, this method results in that the catheter acquires curls in the round shape due to the plastic deformation of the stainless steel wire and the catheter cannot be used in introduction into a blood vessel at the time of procedure. In view of this, the things enveloped into a kit have been limited to small packageable devices, excluding the catheter.

For packaging a long or large-sized medical device, it may be contemplated to enlarge the tray or package itself in size. This approach, however, would leads to the inconveniences in that more room is taken when the devices are stocked in hospitals, that they cannot be completely contained in the refuse bin at the time of discarding them after procedure, and so on. In the method disclosed in Patent Document 1, the catheter as a whole is packaged as it is in a long state, so that the package is large in size, and the devices packaged together with the catheter are limited to thin devices.

Patent Document 1: Japanese Patent Laid-open No. Hei 11-130132

DISCLOSURE OF INVENTION

Problems to be Solved by the Invention

The present invention has been made in consideration of the above-mentioned problems. Accordingly, it is an object of the present invention to provide a catheter package capable of containing a plurality of medical devices and an angiography catheter and the like used for one catheter procedure without increasing the size thereof.

Means for Solving the Problems

The above object can be attained by the present invention as set forth in the followings (1) to (5).

(1) A catheter package packaging a catheter comprising a catheter body having a distal portion and a proximal portion, a tube wall defining a lumen passing through from the distal portion to the proximal portion and a metal reinforce member embedded in the tube wall, and a connector part fixed to the proximal portion of the catheter body, wherein the distal portion of the catheter of 10 to 50 cm in length is held in a natural state with no external force exerted thereon, and the remaining proximal side of the catheter is held in a curled state with a curvature diameter of 10 to 50 cm.

(2) A catheter package as set forth in (1) above, wherein the catheter is an angiography catheter or a PTCA guiding catheter.

(3) A catheter package as set forth in (2) above, wherein the reinforcement member is a stainless steel wire material.

(4) A catheter package as set forth in claim 2 or 3, wherein the distal portion of the catheter has a predetermined curved shape in the natural state thereof.

(5) A catheter package as set forth in any of (1) to (4) above, wherein the catheter is held in the state of astride over two trays separateably integrated with each other.

Effects Of the Invention

As has been described above, according to the catheter package of the present invention, it is possible to facilitate preparatory works, thereby alleviating the burden on the medical workers, and to prevent misuse of devices or the like trouble, at the time of carrying out a catheter procedure.

DESCRIPTION OF REFERENCE NUMERALS

Figure 1:
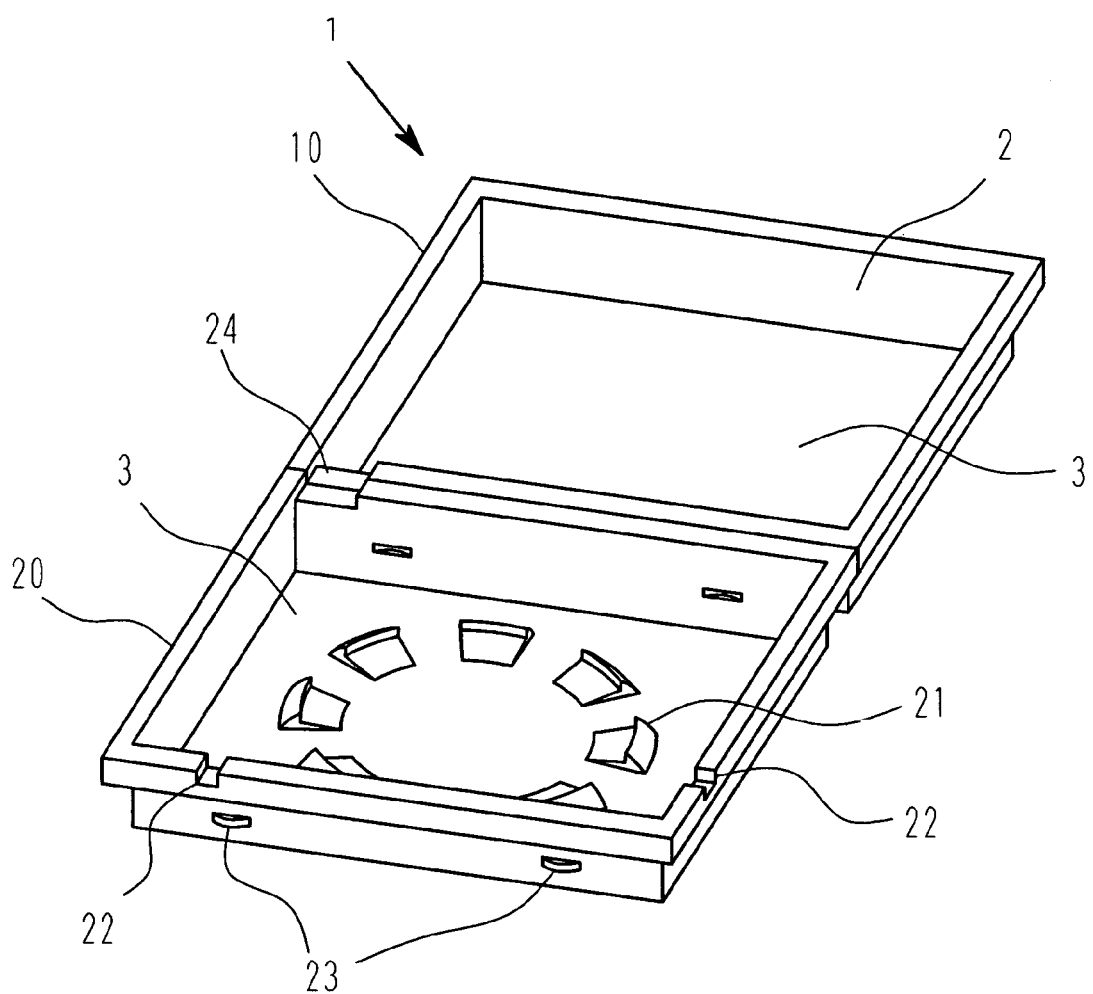
FIG. 1 is a perspective view of an embodiment of a medical device enveloping tray 1 according to the present invention.
Figure 2:
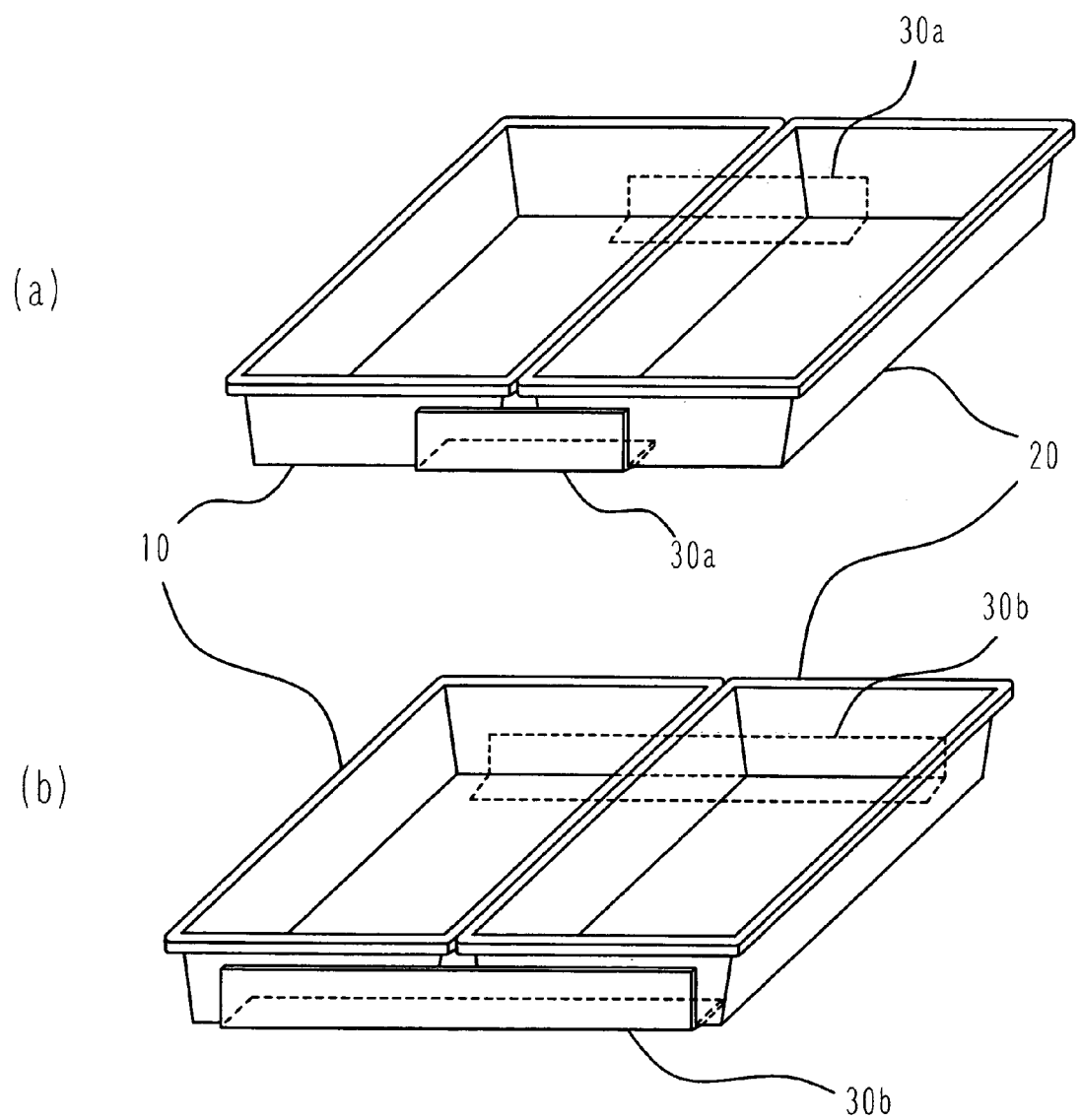
FIG. 2 is a perspective view of a variation of joining between the trays 10 and 20 shown in FIG. 1.

1: tray
2: wall
3: bottom plate
10: first tray
20: second tray
30: fixing member
40: catheter protective cover
50: small tray
60: partition board
100: catheter Best Mode for Carrying Out the Invention Now, the catheter package according to the present invention will be described in detail below, based on the preferred embodiments shown in the accompanying drawings. FIG. 1 is a perspective view of an embodiment of a medical device enveloping tray 1 constituting the catheter package of the present invention.

In FIG. 1, the tray 1 has a first tray 10 and a second tray 20, longer sides of which are joined to each other. Each of the trays 10 and 20 has a rectangular bottom plate 3 having a longer side of about 30 to 70 cm and a shorter side of about 20 to 60 cm, the four sides of which are surrounded by four walls 2 of 3 to 20 cm in height which are formed substantially perpendicularly from the bottom plate 3. The devices to be introduced into a blood vessel such as a catheter, a sheath and a guide wire to be used must be immersed in physiological saline before use, for preventing from air bubbles interfusing into the blood vessel. Since the trays 10 and 20 each have the above-mentioned size and structure in the present invention, the tray can be filled with an appropriate amount of physiological saline. Specifically, if the walls 2 of the tray are absent, the physiological saline cannot be reserved, and if the size of the tray (the area of the bottom plate 3) is too large, a large amount of physiological saline is needed, which is uneconomical. Besides, if the size of the tray is too large, it is inconvenient for discarding it after use.

The tray 20 has the bottom wall provided with a plurality of projections 21 arranged in a circle. The projections 21 have the advantage of restraining a guide wire or the like packaged in a circular form from moving. Since a guide wire is formed from a thin wire material of a superelastic alloy coated with a resin, the guide wire can be packaged in a circularly looped form, since it does not remain the curled form after removing the deforming stress. Besides, the tray 20 is used for immersing an angiography catheter and the guide wire in physiological saline, by pouring the physiological saline therein at the time of a procedure. The projections 21 also function to partition the guide wire and the catheter from each other so as to obviate the possibility that the guide wire and the catheter present in a mixed state might be difficult to take out. Further, the projections 21 each have a substantially vertical wall on the inner side (center side) of the circle, and a gradually inclined surface on the outer side, whereby the guide wire being high in elasticity can be prevented from flying out to the outside of the projections 21, and the guide wire can be easily gripped with the operator's fingers when taken out. In addition, at the time of picking up the catheter placed on the outer side of the circle, the catheter can be easily picked up by sliding along the surface inclined. In addition, the inner side (center side) of the circle has an inclined surface sloping down to the inner side of the circle, at a lower portion of the substantially vertical surface. Therefore, at the time of taking out the guide wire, which ordinarily has a hydrophilic outside surface and is very high in lubricity, from the inner side of the circle, the guide wire may be first lifted up from the bottom plate 3 by pulling it up onto the sloping portions of the projections 21, whereby the guide wire can be easily picked out at a position between the projections 21.

If the projections 21 were provided not in the plurality as above but in the form of a single circular projection, a guide wire placed on the inside of the circle would stick to the inner circumference side of the projection and be difficult to take out. Since the projections 21 have cutouts arranged partly on the circumference of the circle, the guide wire can be easily taken out by putting a finger thereon at the cutout portion.

In addition, the presence of the projections 21 inside the tray makes it possible to immerse the devices in physiological saline by pouring therein the physiological saline in a smaller amount, due to the reduced volume corresponding to the total volume of the projections 21, as compared with the case where the bottom surface of the tray is flat as usual.

Besides, the walls 2 surrounding the tray 20 are provided with a plurality of dents 22 in edge portions thereof. The dents 22 are each configured that a hub at a proximal portion of a catheter can be attached thereto. This ensures that, in the instance of a procedure, a plurality of catheters 100 can be preliminarily set in position and be easily taken out in the order of use thereof. In addition, a dent 24 is provided for permitting a catheter to range over both the trays 10 and 20 when the catheter is packaged as will be described later. The dent 24 is formed by partly decreasing the height of an end portion of the joint surface of the two trays, of the plurality of walls 2, and is dented to have a depth greater than the outer diameter of the catheter. Specifically, the dent 24 is desirably dented to have a depth of not less than 4 mm.

In addition, the wall 2 of the tray 20 is provided with a plurality of projections 23 along a central portion thereof. The projections 23 can be projected to both the inside and the outside of the tray 20 by pushing with a finger. At the time of immersing a catheter 100 in physiological saline inside the tray 20, the projections 23 are projected to the inside of the tray 20 so as to prevent the catheter 100 from flying out to the exterior of the tray. At the time of discarding the physiological saline and used devices after a procedure is finished, the projections 23 are projected to the outside of the tray 20, whereby they can be prevented from hampering the discarding work.

The trays 10 and 20 are formed from a resin material having a desired strength, such as ABS, AES, PC, PP, PE, PS, HIPS, PET, PVC, etc. by a manufacturing method such as vacuum forming, air-pressure forming, press molding, etc.

FIGS. 2 to 6 show variations of the manner of joining between the trays 10 and 20 shown in FIG. 1. In each of the embodiments shown in FIGS. 2 to 6, the trays 10 and 20 are fixed to each other by a fixing member 30(a to f). Though the fixing member 30 may be single, the two trays can be fixed to each other more firmly when a plurality of fixing members are provided.

In the embodiment shown in FIG. 2(a), fixing members 30a are each composed of an L-shaped plate member making close contact with the bottom and side surfaces of the two trays 10 and 20 disposed adjacently, and are formed from a metal or hard plastic material. The fixing member 30a is adhered to the side and bottom surfaces of the trays by a pressure sensitive adhesive tape or the like, whereby the trays 10 and 20 are firmly fixed so as not to be separated from each other during transportation. Incidentally, a pressure sensitive material such as a double faced pressure sensitive adhesive tape may be disposed on the inside of the fixing member 30a.

The embodiment shown in FIG. 2(b) differs from the embodiment shown in FIG. 2(a) only in that the width of fixing members 30b is so set as to substantially cover the sum of the shorter sides of the trays 10 and 20.

Figure 3:
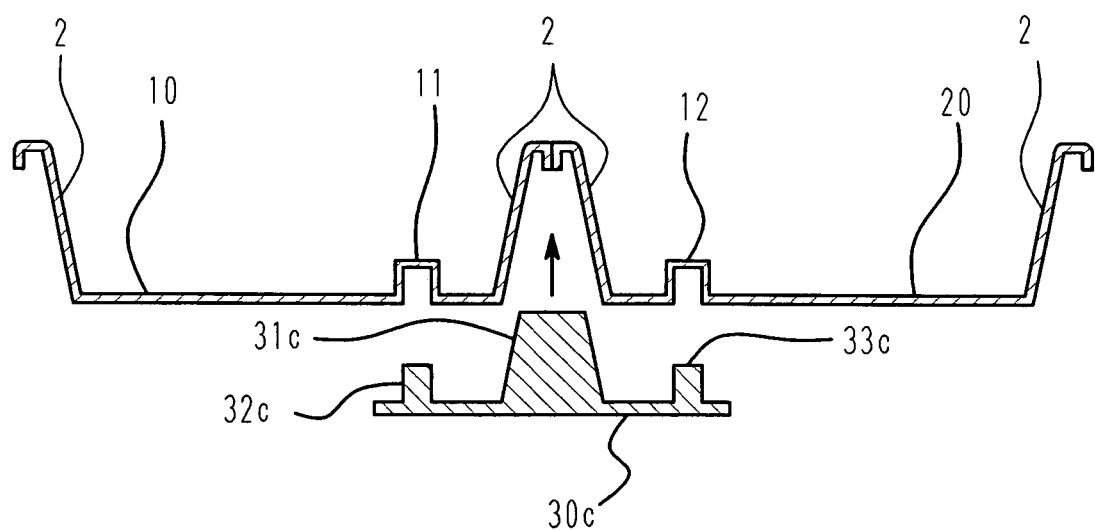
FIG. 3 is a cross-sectional view of a variation of joining between the trays 10 and 20 shown in FIG. 1.

FIG. 3 shows, in section, the relationship between the trays 10, 20 and a fixing member 30c. In the embodiment shown in FIG. 3, the fixing member 30c has three projections, namely, a central projection 31c and left and right projections 32c and 33c. The central projection 31c is inserted between the trays 10 and 20. In the trays 10 and 20, the walls 2 are inclined for convenience in use or convenience in forming. Specifically, the walls 2 are inclined to the outside so that the area of each of the trays 10 and 20 is larger on the upper side than at the bottom plate 3. In addition, each wall 2 is provided at its top portion with an outside bent-back part (edge) for strengthening and safety at the time of holding by hand. Therefore, when the trays 10 and 20 are aligned so that their longer sides make contact with each other, the bent-back parts of the walls 2 make contact, with result that a gap corresponding to the two bent-back parts is generated on the upper side between the trays, while a gap corresponding to the two bent-back parts plus the two inclinations of the walls 2 is generated on the lower side between the trays. The projection 31c of the fixing member 30c is formed in a shape for engagement with such a gap.

In addition, the left and right projections 32c, 33c are formed in shapes for engagement with recessed parts 11 and 12 formed in the bottom plates 3 of the trays 10 and 20, respectively. In the condition where the trays 10 and 20 are aligned, two fixing members 30c are attached to the two trays from both sides, whereby the two trays are fixed and can maintain their integrated state during transportation and use. Incidentally, the fixing members 30c can be fixed to the bottom plates 3 of the trays more firmly by use of pressure sensitive adhesive tapes (not shown) or the like. Incidentally, the central projection 31c can be omitted when the walls of the trays 10 and 20 are made to be perfectly vertical.

Figure 4:
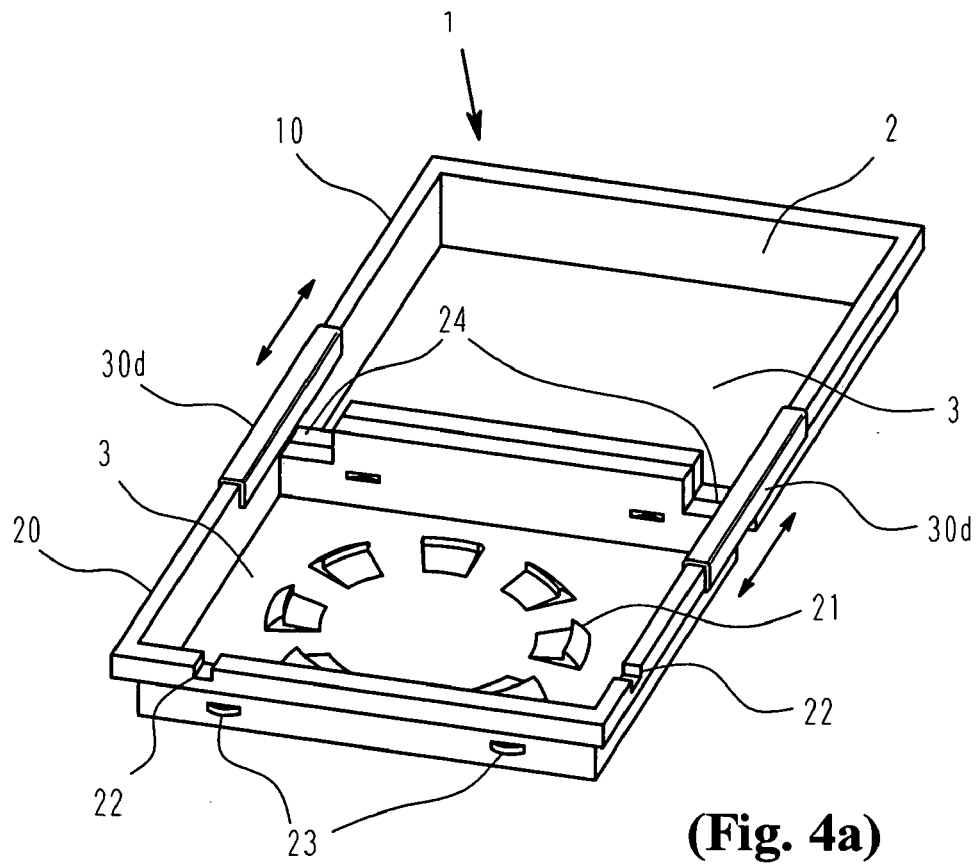
FIG. 4 is a view of a variation of joining between the trays 10 and 20 shown in FIG. 1.
Figure 4:
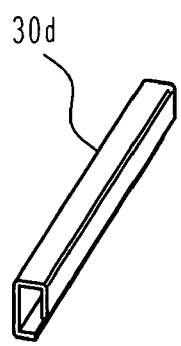
Figure 4:
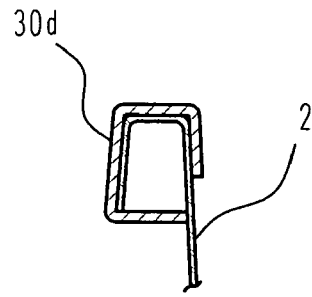

FIG. 4 illustrates another embodiment as to the method of fixing two trays. FIG. 4a illustrates the condition where fixing members 30d according to this embodiment is attached to the trays, FIG. 4b shows the fixing member 30d singly, and FIG. 4c is a sectional view of the fixing member 30d in its state of being attached to the trays. The fixing members 30d are slidably fitted over the bent-back parts at upper portions of the walls 2 of the trays. Each of the fixing members 30d has four surfaces, one of which is partly cut out so that the wall 2 of the tray can be received to the inside thereof through the cutout and can be fitted therein. As shown in section in FIG. 4c, the fixing member 30d is fitted over the wall 2 of the tray so as to hold three surface, namely, the inside (inside the dent 24) of the tray, the upper surface of the wall 2, and the outside of the bent-back part of the wall 2; therefore, the fixing member 30d can be slid on the walls 2 in the directions indicated by arrows in FIG. 4a, and can be firmly fitted in position so as not to slip off easily. In addition, the same fixing members 30d are disposed at left and right two positions. Further, the dent 24 of the wall 2 of the tray is also provided in two places.

According to the embodiment shown in FIG. 4, at the time of integrating the two trays, the fixing members 30d are each disposed ranging over the boundary part (i.e. the portion of the dent 24) of both the trays, so as to firmly fix both the trays. At the time of separating the trays from each other in use or for discarding, it suffices to slide the fixing members 30d to the side of one of the trays; thus, a configuration very excellent in convenience in use is realized.

Figure 5:
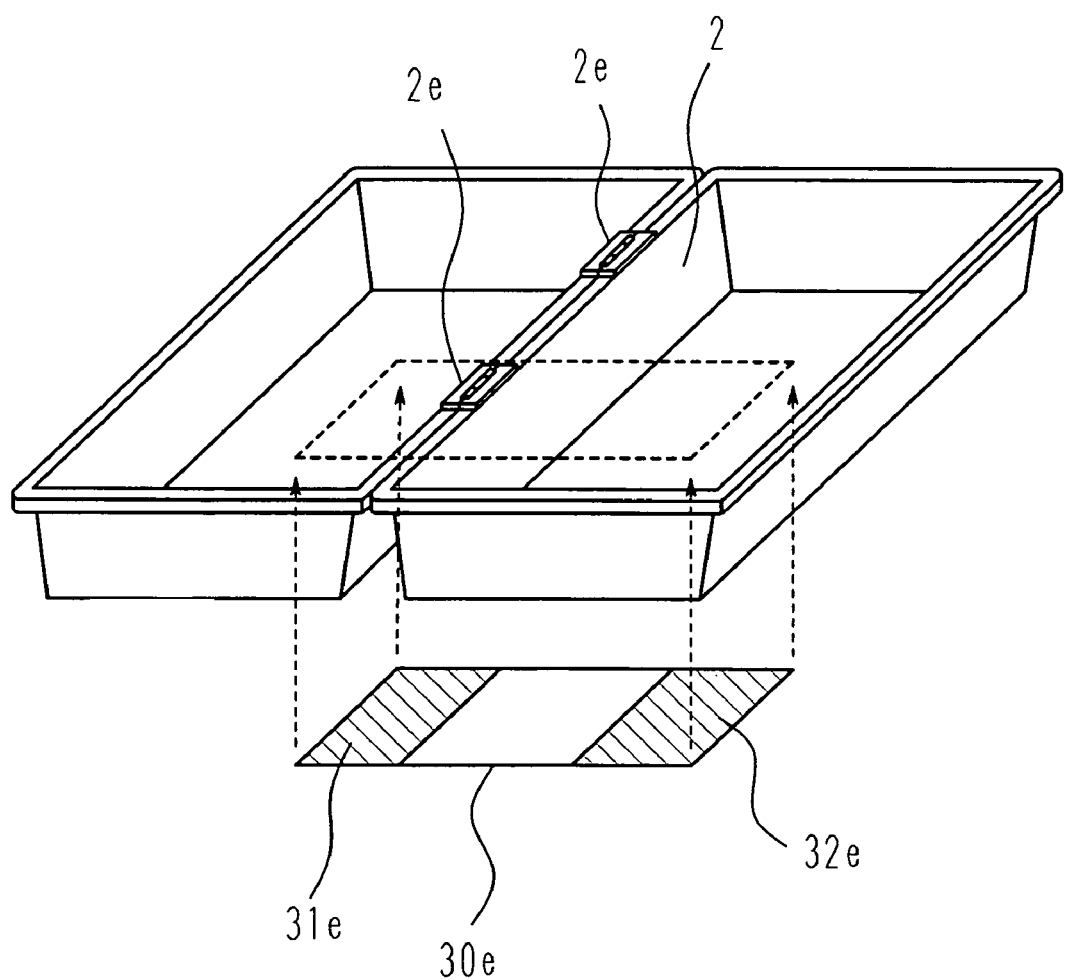
FIG. 5 is a perspective view of a variation of joining between the trays 10 and 20 shown in FIG. 1.

In the embodiment shown in FIG. 5, the edges of the longer side walls 2 of the trays 10 and 20 are turnably integrated at two pivotal parts 2e. As the integrating means, there can be used not only hinge-type pivotal parts 2e, but also a method in which the edges of the trays are provided with cylindrical parts in an alternate manner and a metal shaft or the like is passed through the cylindrical parts to form a hinge, or a method in which the edges of the trays are turnably connected to each other by a pressure sensitive adhesive tape. In this embodiment, the trays 10 and 20 are preliminarily integrated with each other, so that a fixing member 30e is not demanded to have a high holding force, and can be composed of something like a pressure sensitive adhesive tape. In the figure, the portions denoted by 31e and 32e are pressure sensitive adhesive portions. In this embodiment, at the time of discarding the trays 10 and 20, the turnable parts 2e are turned to lay the edges of the two trays on each other, whereby a reduction in size can be achieved. Therefore, it is also possible to discard the used medical devices used left in the trays during a procedure, in the state of being sealed in the inside of the two trays.

Figure 6:
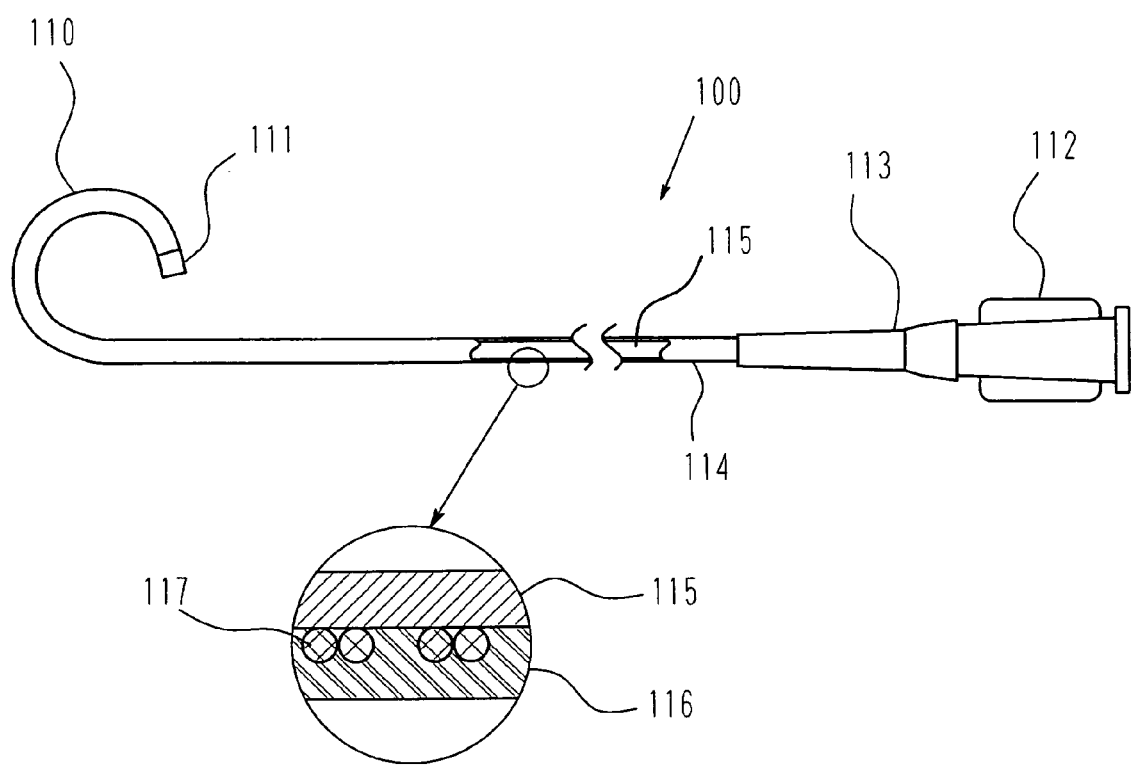
FIG. 6 is an elevational view of an angiography catheter 100.

FIG. 6 shows the configuration of an angiography catheter 100 packaged in the present invention. The catheter 100 has a connector part 112 provided at the proximal end of a tubular body having a lumen 115 passing through from a distal portion 110 to a proximal portion 114 of the tubular body, and an anti-kinking protector 113 for preventing kinking of the catheter is provided on the tip side of the connector part 112.

The distal portion 110 has a curved part e.g. the so-called pig tail shape at its tip, for the purpose of enhancing the selection performance of the distal portion introduced into a blood vessel at a branching portion of the blood vessel at the time of introduction, or for the purpose of efficiently distributing an angiography contrast medium for obtaining the image of a blood vessel under fluoroscopy. Besides, a very flexible distal tip 111 is provided at the most distal end of the catheter 100, for the purpose of protecting the inside wall surface of the blood vessel.

Shown in a circle in FIG. 6 is an enlarged sectional view of the tube wall constituting the body of the catheter 100. The tube wall has a two-layer structure composed of an inner layer 115 and an outer layer 116, in which braids 117 of metal wire such as stainless steel wire as a reinforcement member are embedded in pairs and in a total number of 32. The braids 117 are for enhancing torque transmission performance and kink resistance at the time of manipulating the catheter inside a blood vessel from the proximal portion 114 side. The metal wire used for such a braid is formed of an inexpensive material such as stainless steel. Since stainless steel is highly susceptible to plastic deformation and curling, it has conventionally been held straight on a mount paper when packaged.

Figure 7:
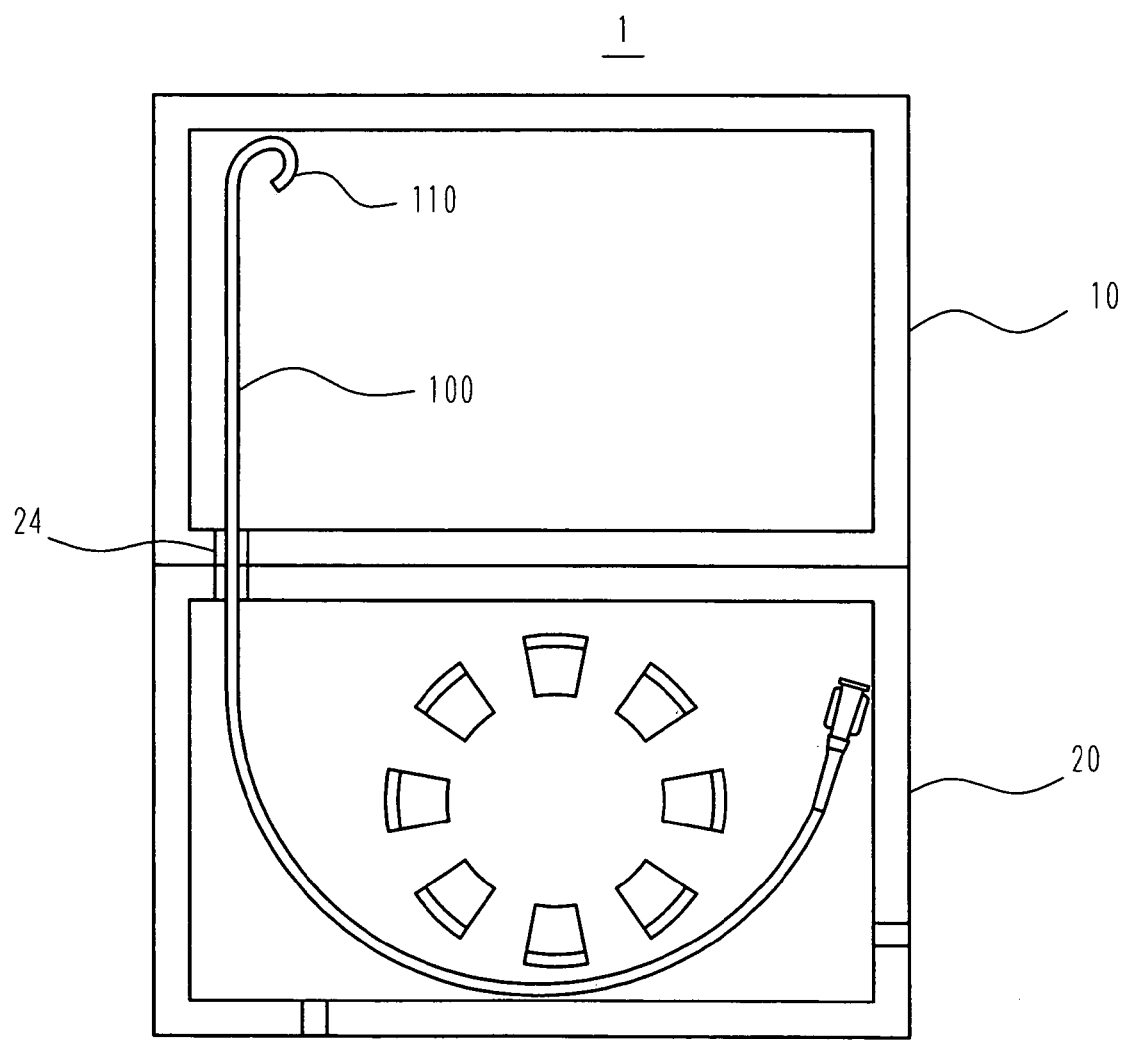
FIG. 7 is an elevational view of the manner in which the angiography catheter 100 is laid out in the tray 1 shown in FIG. 1.

FIG. 7 shows the manner in which an angiography catheter 100 is disposed in the tray 1 shown in FIG. 1. Although the manner in which one catheter 100 is disposed is shown in FIG. 7, a suitable catheter distal shape varies depending on the blood vessel to be imaged in a catheter procedure, so that about two or three catheters different in distal shape may be used in one procedure, or guiding catheters for the therapy catheter may be enclosed. In the present invention, therefore, a plurality of long catheters 100 may be enclosed in the tray 1 together. In enclosing a plurality of catheters, the catheters may be disposed in parallel and close to each other or be bundled.

At the time of disposing the catheter 100 on the tray, it is desirable to maintain the distal part of the catheter 100 of 10 to 50 cm in length from the tip in a natural state with no external force exerted thereon (the curved distal portion is in the curved shape, the other portion is in a straight state), for keeping the distal shape and maintaining the operationality such as torque transmission performance. Therefore, the straight holding part is preferably disposed in the shape along the shorter side wall of the tray 10. In addition, the remaining proximal side part of the catheter 100, particularly, of 10 to 100 cm in length is disposed in a curled state so as to be well contained within the tray 20. The diameter of curvature in this curl is preferably in the range of 10 to 50 cm, more preferably in the range of 15 to 35 cm. If the diameter of curvature is more than 50 cm, the size of the tray would be too large, which is unfavorable; on the other hand, if the diameter of curvature is less than 10 cm, a deformed curl exceeding a permissible level would be generated, which is also unfavorable. These fears can be obviated more assuredly when the diameter of curvature is within the range of 15 to 35 cm. The part of the catheter 100 ranging between the trays 10 and 20 is disposed in the dent 24 provided in the walls 2 of the trays 10 and 20.

Figure 8:
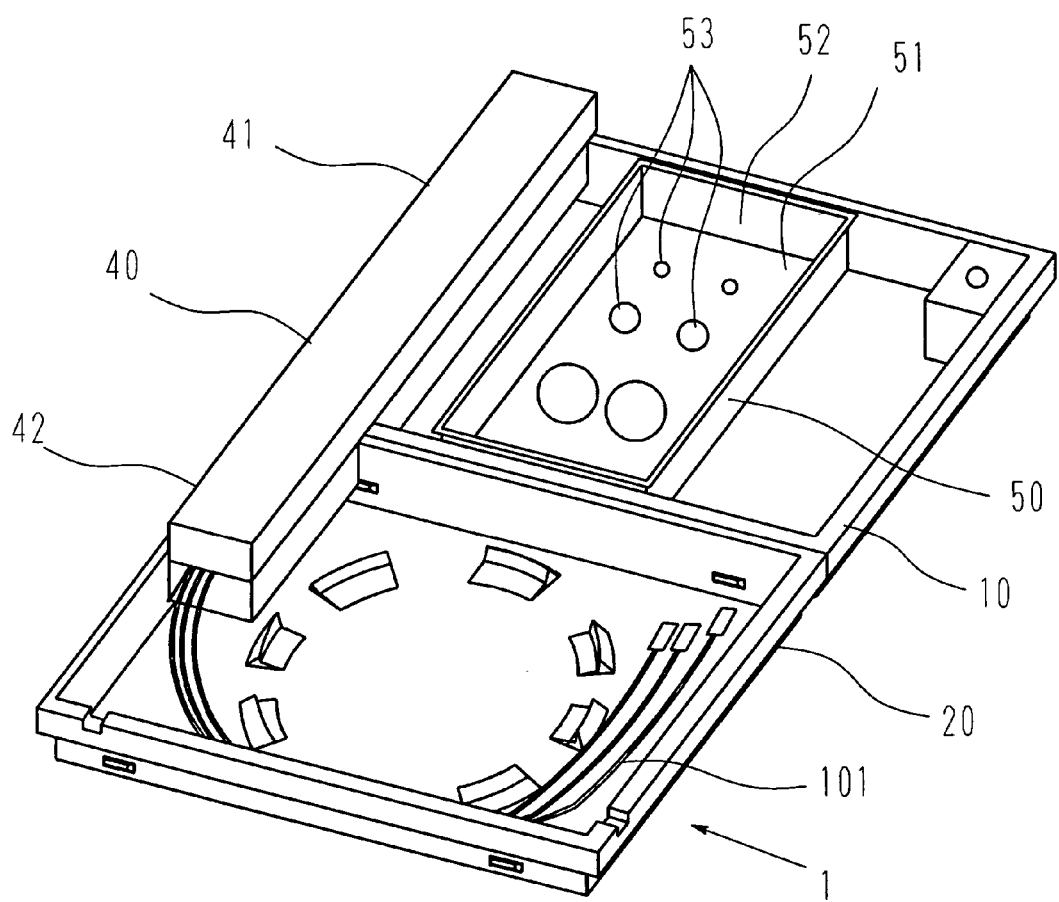
FIG. 8 is a perspective view of the manner in which the tray 1 shown in FIG. 1 is equipped with a catheter protective cover 40 and a small tray 50.

FIG. 8 shows the condition where a catheter protective cover 40 for protecting the distal portions of the catheters 100 and a small tray 50 are disposed in the tray 1. The catheters 100 are flexible and small in diameter so as to be insertable in a blood vessel, and it is therefore susceptible to kinking and bending; accordingly, the catheters 100 must be protected so that it would not be collapsed by other devices enveloped together therewith in the tray during transportation. In this embodiment, the catheters 100 are disposed ranging over both the two trays 10 and 20, so that the protection of its part ranging between the two trays is also important. In addition, in the case where the catheters 100 are provided with a three-dimensional shape at its distal part, the protection of the distal portion is also important. In view of these points, the catheter protective cover 40 is made to be a box-like or tubular cover, to function as a three-dimensional cover for covering and protecting a part of the catheter.

The catheter protective cover 40 is composed of a box-like part 41 with a comparatively broad internal space for covering the distal shape parts of the catheters 100, and a box-like part 42 with a comparatively narrow internal space ranging between the two trays 10 and 20. The box-like parts 41 and 42 have mutually communicating internal passages through which the catheters 100 can be passed, and are set ranging over both the trays 10 and 20 with the distal portions of the catheters 100 disposed therein. Here, in order to protect the catheters 100 more assuredly, the catheters 100 to be disposed in the inside of the catheter protective cover may be disposed after being preliminarily set on a mount paper, not shown, or the like.

The small tray 50 is composed of a rectangular bottom surface 51 and walls 52 surrounding the four sides of the bottom surface 51, and is provided so as to prevent comparatively small medical devices such as syringes and needles from being scattered during conveying.

Figure 9:
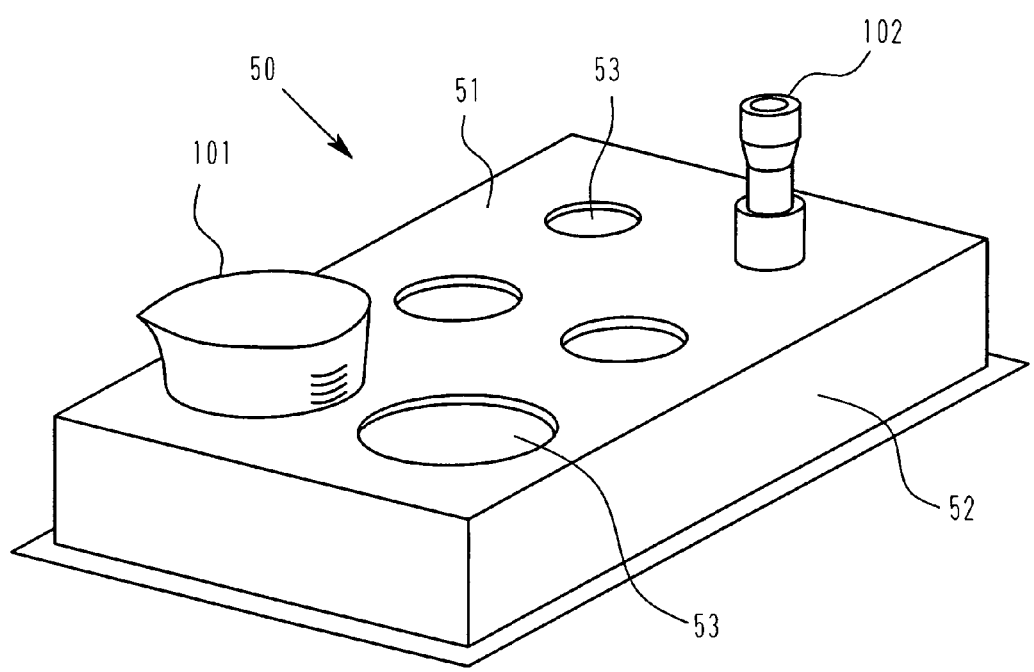
FIG. 9 is a perspective view of the condition where the small tray 50 is inverted upside down.

The bottom surface 51 of the small tray 50 is provided with a plurality of large and small holes 53. When a procedure begins, the small tray 50 is turned upside down so that the bottom surface 51 assumes the position of a ceiling plate. In this condition, as shown in FIG. 9, the small tray 51 can be utilized as a member for holding a beaker 101, a needle 102, a syringe and the like upright by placing them in the holes 53.

Figure 10:
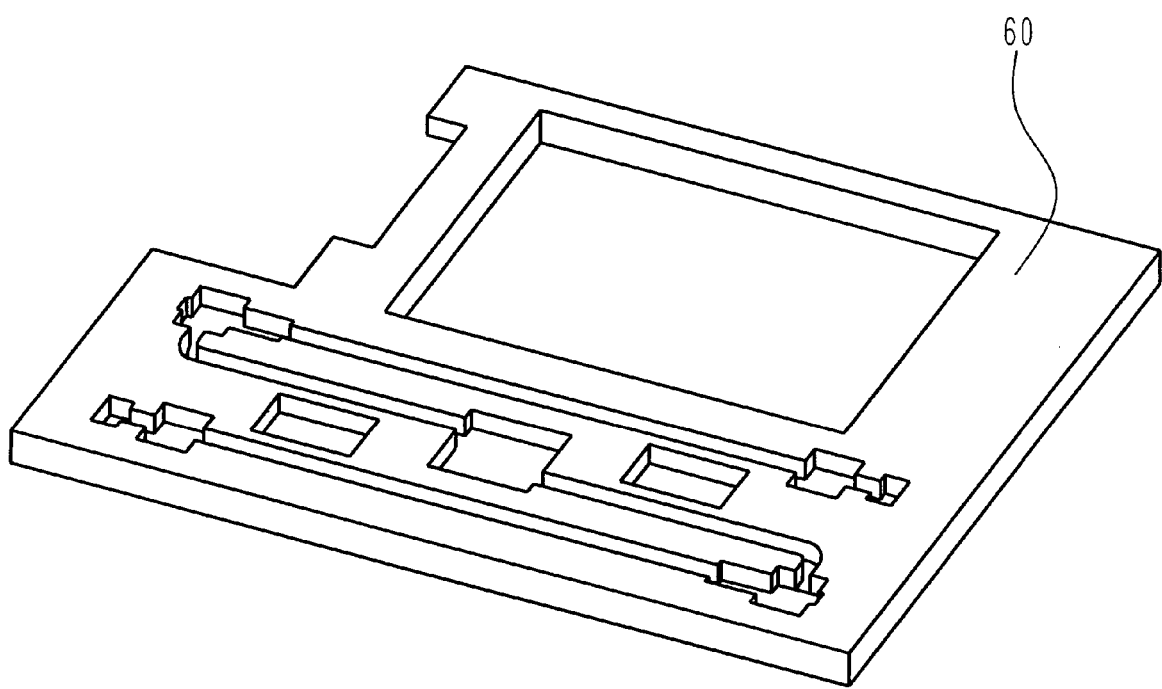
FIG. 10 is a perspective view of a partition board 60 which is placed in the tray 20.

FIG. 10 shows a partition board 60 to be disposed in the tray 20. The partition board 60 is provided so that the catheters 100 and the guide wire disposed on the bottom surface of the tray 20 would not be collapsed by other devices packaged on the upper side thereof, during conveying.

The partition board 60 is formed from a resin sheet three-dimensionally, and is provided with a plurality of hollows in its surface. Formed in such a shape, the partition board 60 can also function as a member on which medical devices are fixed. Specifically, a plurality of introducer sheaths, dilators, indwelling needles, guide wires for the introducers and the like to be used in a procedure before using the catheters 100 and the guide wire are set on the partition board 60. With such a configuration, the devices to be used in a stage before a procedure, such as a procedure clothing, gloves, a drape, instillation devices, etc. are disposed on the upper side of the partition board 60, such devices as introducers to be used in the beginning of the procedure are disposed on the partition board 60 itself, and the guide wire and the catheter 100 to be used in the later stage of the procedure are disposed on the lower side of the partition board 60, whereby the devices can be taken out following the order of use, which promises a very high utility.

The invention claimed is:

1. A catheter packaged in a catheter package, the catheter package comprising two trays, each tray comprising a bottom and upstanding sidewalls, the catheter comprising a catheter body having a distal portion and a proximal portion, a tube wall defining a lumen passing through from the distal portion to the proximal portion and a metal reinforce member embedded in the tube wall, and a connector part fixed to the proximal portion of the catheter body, wherein the catheter package holds the distal portion of the catheter of 10 to 50 cm in length in a natural state with no external force exerted thereon, and the catheter package holds the remaining proximal side of the catheter in a curled state with a curvature diameter of 10 to 50 cm, wherein the catheter is held astride over the two trays, the two trays being integrated with each other by at least one fixing member, and wherein the at least one fixing member is slidably fitted over the sidewalls of the two trays.

2. The catheter of claim 1, wherein the catheter package comprises a plurality of independent trays, an upstanding sidewall of one of the plurality of trays being in back-to-back relationship with an upstanding sidewall of an other of the plurality of trays.

3. The catheter of claim 2, wherein a cutout extends through the back-to-back upstanding sidewalls, a portion of the catheter being positioned in the cutout.

* * * * *